US 6,406,458 B1

(12) United States Patent
Tillander

(10) Patent No.: US 6,406,458 B1
(45) Date of Patent: Jun. 18, 2002

(54) PRESSURE INFUSION APPARATUS

(75) Inventor: Hans Tillander, Göteborg (SE)

(73) Assignee: Premetec AB, Vastra Frolunda (SE)

( * ) Notice: Subject to any disclaimer, the term of this patent is extended or adjusted under 35 U.S.C. 154(b) by 0 days.

(21) Appl. No.: 09/011,444

(22) PCT Filed: Aug. 9, 1996

(86) PCT No.: PCT/SE96/01007

§ 371 (c)(1),
(2), (4) Date: Feb. 9, 1998

(87) PCT Pub. No.: WO97/05915

PCT Pub. Date: Feb. 20, 1997

(30) Foreign Application Priority Data

Aug. 9, 1995 (SE) .............................................. 9502789

(51) Int. Cl.[7] .............................................. A61M 37/00
(52) U.S. Cl. ....................................... 604/147; 604/246
(58) Field of Search ............................... 604/141, 147, 604/131, 246; 222/92, 95

(56) References Cited

U.S. PATENT DOCUMENTS 3,640,277 A * 2/1972 Adelberg
5,308,335 A * 5/1994 Ross et al.
5,700,245 A * 12/1997 Sancoff et al.

FOREIGN PATENT DOCUMENTS

| DE | 2053995 | 5/1972 |
| DE | 2246054 | 4/1973 |
| DE | 2731448 | 1/1978 |
| SE | 448822 | 3/1987 |
| SE | 467951 | 10/1992 |
| WO | WO89/11303 | 11/1989 |

* cited by examiner

Primary Examiner—Mark Bockelman
(74) Attorney, Agent, or Firm—Merchant & Gould P.C.

(57) ABSTRACT

Pressure infusion apparatus (10) of the type that includes a chamber (13) for at least one infusion bag (21). In the chamber a pressure apparatus (18) applies pressure on the infusion bag to press out infusion liquid through an infusion tube (24). The pressure apparatus (18) includes a pneumatic pressure chamber (25) and a pressure source (27). Between the pressure storage chamber (25) and the pressure source (27) there is a pressure reduction valve (26) that significantly reduces the pressure in the pressure source (27) relative to the maximum loading pressure in the pressure storage chamber (25). The pressure source (27) includes an essentially unstretchable, air tight, flexible membrane (27a) which divides the chamber (13) into an infusion chamber and a pressure chamber (27b) and which presses directly on the bag (21). At least one flow regulating valve (28) giving a calibrated flow per unit time is attached to the infusion tube (24) or its extension from the infusion bag (21).

9 Claims, 5 Drawing Sheets

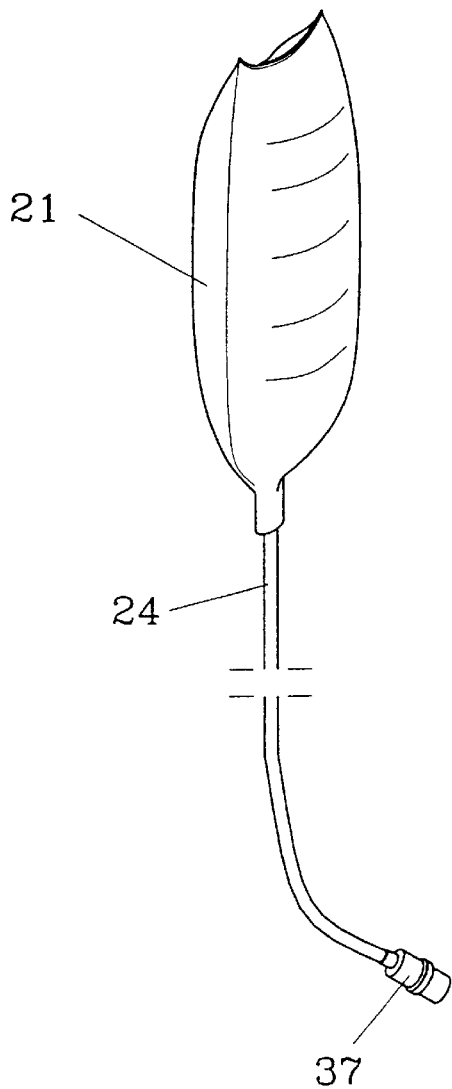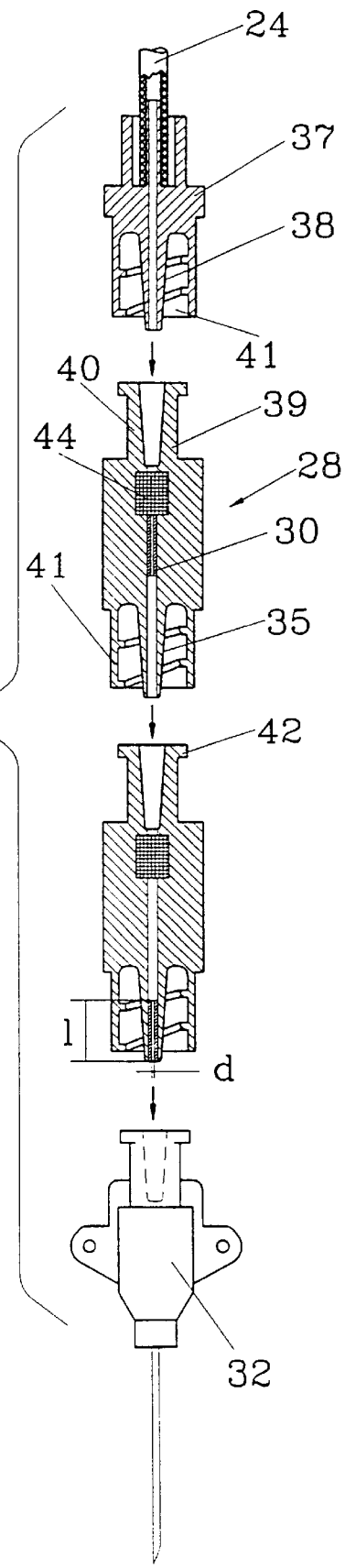
FIG. 7
FIG. 8

PRESSURE INFUSION APPARATUS

TECHNICAL FIELD

The present invention concerns a pressure infusion apparatus of the type that includes a chamber for receiving at least one infusion bag and in which chamber there is a pressure apparatus operating against the infusion bag for dispensing the infusion liquid through an infusion tube whereby the pressure apparatus includes a pneumatic pressure storage chamber and a pressure applicator.

DESCRIPTION OF THE KNOWN ART

In connection with acute illness and accidents as well as for therapeutic purposes one often uses intravenous (direct into a blood vessel) injection of liquids in modern medicine. It is an essential step in the prevention of post operative shock. In modern clinical practice glass bottles have long since been abandoned in favor of plastic bags. The latter are lighter, easier to store, better for the patient and superior from the point of view of handling. Nowadays the liquid is almost always stored in plastic bags.

The most usual method of applying the liquid intravenously is to hang up the bag on a support about a meter over the patient and to bring the liquid from the bag to the needle in the vein, usually placed in the arm, via a plastic tube. The flow is regulated by a flow reduction apparatus in the tube and the amount of liquid is controlled by observation of the drop rate in a drop chamber higher up in the tube.

Experienced staff usually know about which drop rate corresponds to a given amount of liquid per unit time. The precision of their judgement is naturally quite variable but great precision is usually not needed. The system usually requires repeated checks during the period of the infusion. When the supply of liquid is to be given to upright patients they have to carry the drop support with them. The same is true for long term nutrition via a tube to the digestive tract.

The technique of compressing bags filled with liquid to dispense liquid is well known in medical applications. There are several different constructions with spring loaded pistons that apply pressure to the bag for that purpose. There are constructions with inflatable rubber balloons which compress the bag for the same purpose. The latter construction requires repeated addition of air pressure, which can be achieved in different ways.

In all cases the mechanical constructions are designed for especially adapted bags which must therefore be marketed together with their contents. This in combination with unsatisfactory flow regulation, mainly based on pressure gradients, and the lack of harmony in the design, at least from the patient's point of view, means that these new creations have not found wide use in health care.

When a more exactly regulated liquid dosage is required, for instance for giving diluted, potent medicine, cell poisons and the like, these systems are not good enough. Then electronic apparatus is used in which a tube pump function or specially attached pumps on the output tube allow a regulated, programmable very exact dosage. These apparatus are expensive, complicated, require electric power and often require expensive accessories for their function. They are also placed on supports, either freely, on rollers or fixed to the patient's bed. They are far too expensive to be used in daily routine applications and are not appropriate for treatment of large numbers of patients, for example in the case of catastrophes.

The Swedish publication text nr 467 951 shows an infusion apparatus consisting of an infusion bag and on it a normally permanently fixed infusion tube including an opening tool and a flow indicator, a clip and a stop valve which prevents return flow to the bag. In use the infusion apparatus is placed under the patient to provide pressure.

The Swedish publication text nr 448 822 shows a portable apparatus including a spring for providing liquid at constant pressure for medical or other similar applications. The spring exerts a constant force moment whereby sticking due to possible twisting of the sliding piece on which the spring exerts its force is eliminated.

Also WO 89/11303 shows an apparatus including a spring which exerts an axial force on a vessel containing a liquid in order to squeeze out the liquid.

The German Publication text 2053995 shows a system including a lower and an upper pressure plate which can be provided with a rubber band around the plates to press them together whereby pressure is applied to an infusion bag placed between the plates so that the liquid is squeezed out of the bag.

The purpose of the invention and the solution of the problem

The purpose of the present invention is to achieve an infusion apparatus which does not depend on an external source of energy, for which no one need hold the liquid containing bag in acute situations, for which there is no drop support, in which the amount of liquid to be given the patient per unit time is easily adjusted, in which the liquid flow is constant during the infusion making checks and adjustments unnecessary, in which air is absent from the system, thus eliminating air bubbles, which is simple and robust and requires few instructions making it especially appropriate in connection with large catastrophes when many people must be treated at the same time, the price of which is kept low through use of disposable material.

The apparatus can also be used for continuous application of nutrition to the digestive tract through a thin tube.

These purposes have been achieved by placing a pressure reduction valve between the pressure storage chamber and the pressure source thus significantly reducing the pressure in the pressure source relative to the maximum loading pressure in the pressure storage chamber, by equipping the pressure source with an essentially unstretchable, air tight, bendable membrane dividing the chamber into an infusion chamber and a pressure chamber acting directly on the bag, and by making it possible to attach a flow regulating valve giving a calibratable flow per unit time to the infusion bag's infusion tube or its extension.

BRIEF DESCRIPTION OF THE DRAWINGS

The invention will be described in greater detail in the following with reference to exemplifications shown in the attached drawings.

FIG. 7 shows in perspective an infusion bag to which a tube is attached.

FIG. 8 shows on a larger than natural scale a cross section through the coupling apparatus of the infusion bag, two valves coupled in series according to the present invention and a infusion needle that can be attached to them.

DESCRIPTION OF THE EXEMPLIFICATIONS

Figure 1:
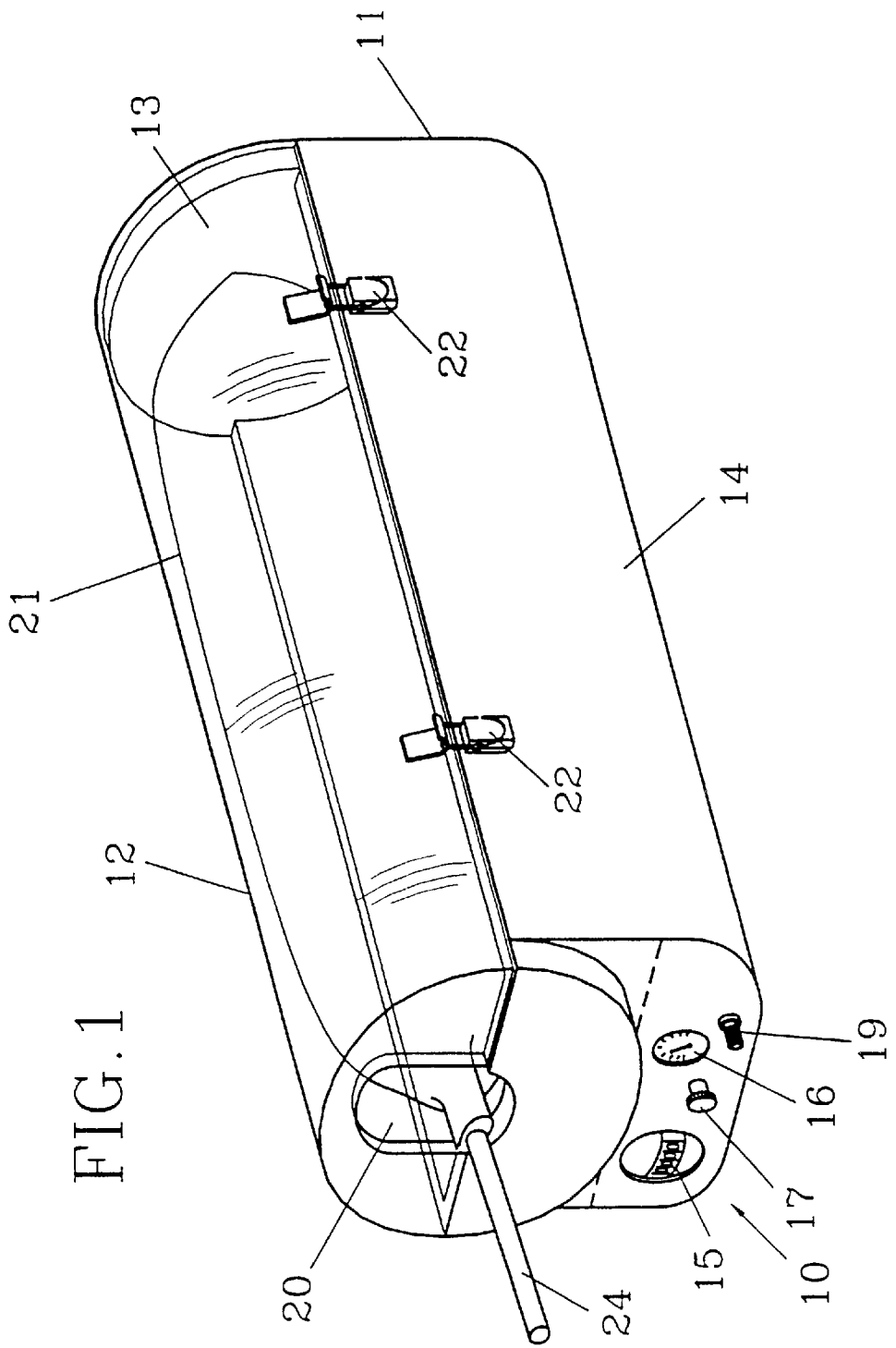
FIG. 1 is a perspective view of the infusion apparatus according to the present invention.

The pressure infusion apparatus 10 shown in FIG. 1–5 includes a housing 11 consisting of a chamber 13 with a top 12 for an infusion bag 21 and below it a vessel 14 which contains part of a pressure apparatus 18. At one end of the housing 11 there is an instrument panel including further parts belonging to the pressure apparatus 18, namely a flow meter 15, a pressure indicator, for instance a pressure gauge 16, a close off valve 17 and a connection nipple 19, which parts will be described in greater detail below. At the same end the top 12 has a slit 20 through which the output tube 24 of the infusion bag is inserted.

The top 12, preferably made of a transparent plastic material with a semicircular cross section, is attached to the lower part of the housing on hinges 31 (FIG. 3) on one long side and can be made fast with locks 22, for example eccentric locks, on the other long side.

Figure 2:
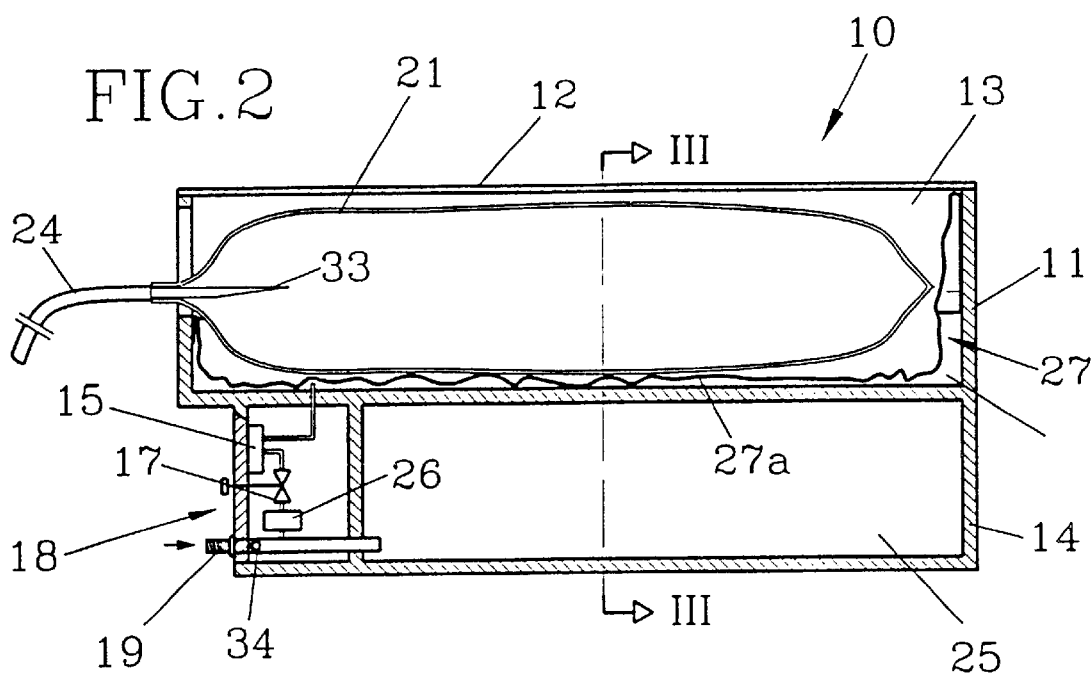
FIG. 2 shows schematically a cross section through the infusion apparatus according to FIG. 1 with the pressure source in the compressed state.
Figure 3:
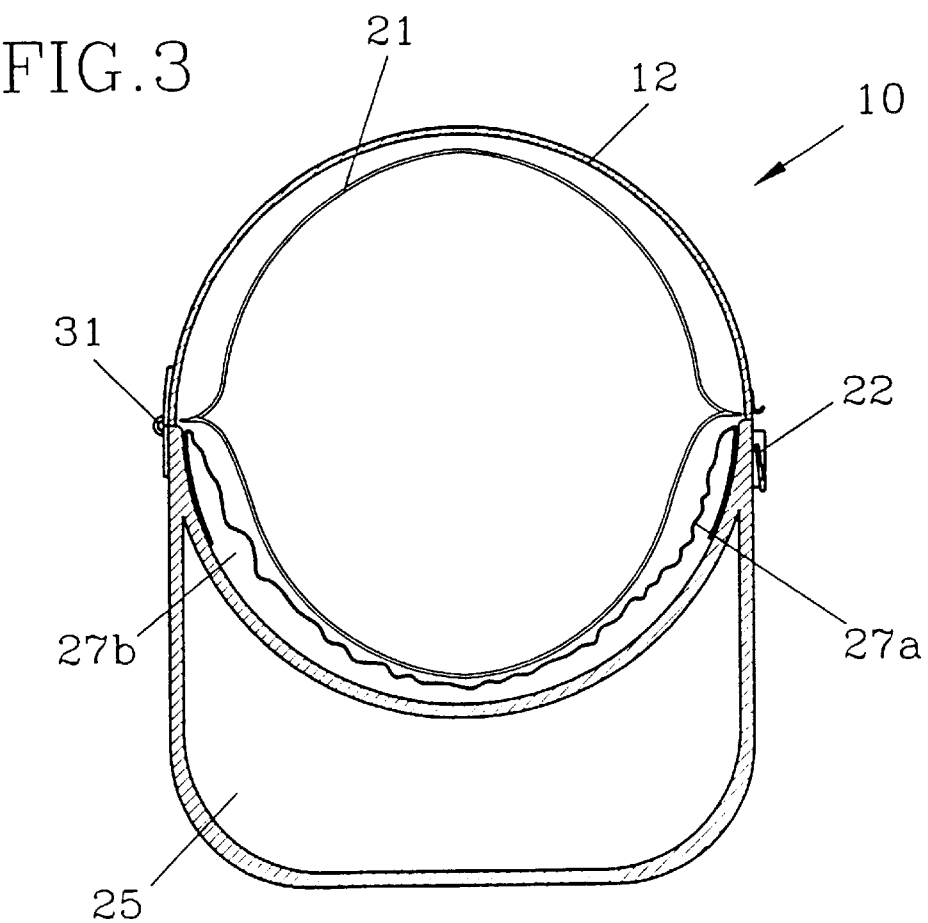
FIG. 3 shows a cross section along the line II–III in FIG. 2 on a larger scale.

FIG. 2 and 3 show schematically a cross section through the exemplification shown in FIG. 1. As is clear from the figures in the chamber 13 there is a pressure source 27 which consists of a membrane 27a or similar thing which divides the chamber 13 into an infusion chamber 13a and a pressure chamber 27b. The membrane 27a is made of a supple, flexible air tight material, for example a cloth, which essentially cannot be stretched but which is so large that in the passive state it lies against the bottom of the chamber and in the stretched state it presses against the inside of the top. The pressure chamber 27b of the pressure source 27 is thus formed by the said membrane 27a and the bottom and side walls of the pressure chamber.

Figure 4:
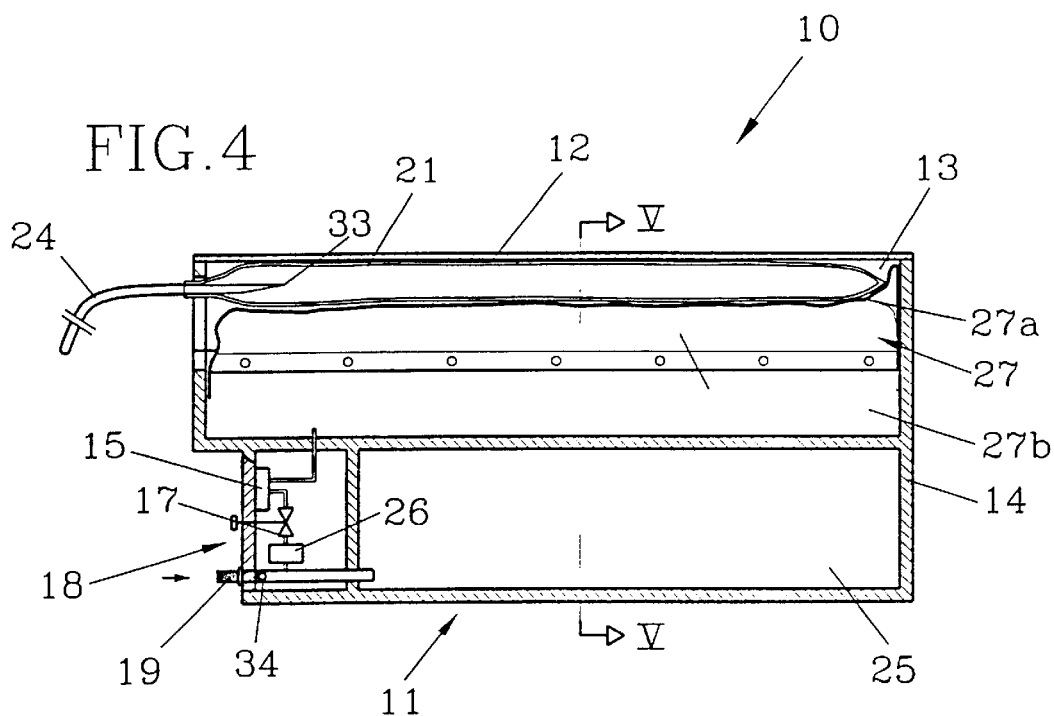
FIG. 4 shows schematically a cross section through the infusion apparatus according to FIG. 2 with the pressure source in the pumped up state.
Figure 5:
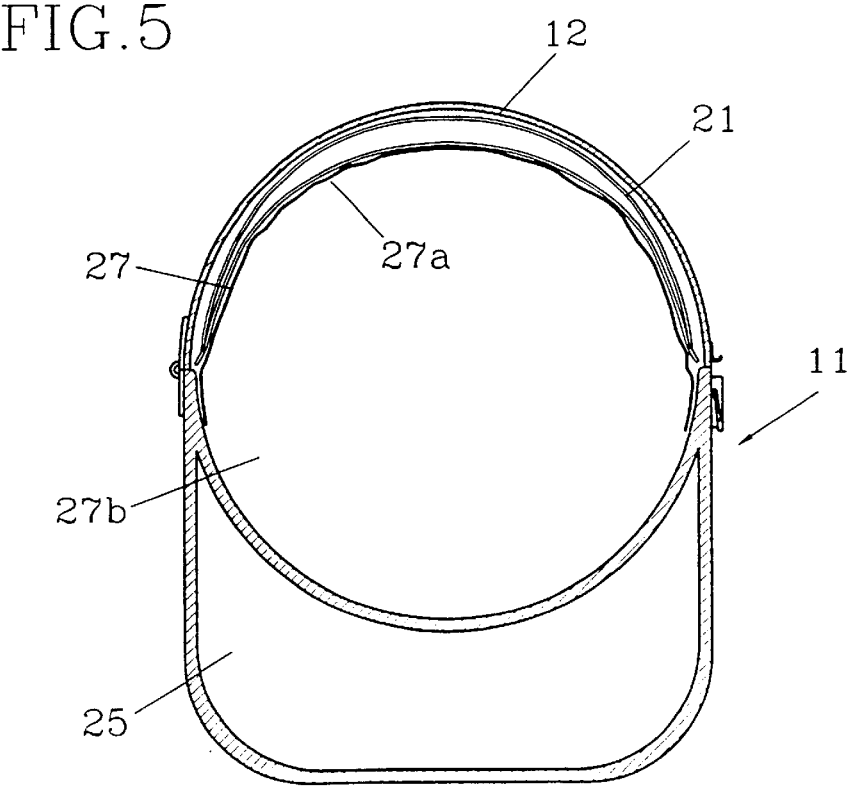
FIG. 5 is a cross section on a larger scale along the line V—V in the apparatus shown in FIG. 4.

FIG. 4 and 5 show the infusion apparatus illustrated in FIG. 2 and 3 but with the membrane 27a of the pressure source 27 inflated and with the infusion bag 21 in the compressed, almost empty state.

Figure 6:
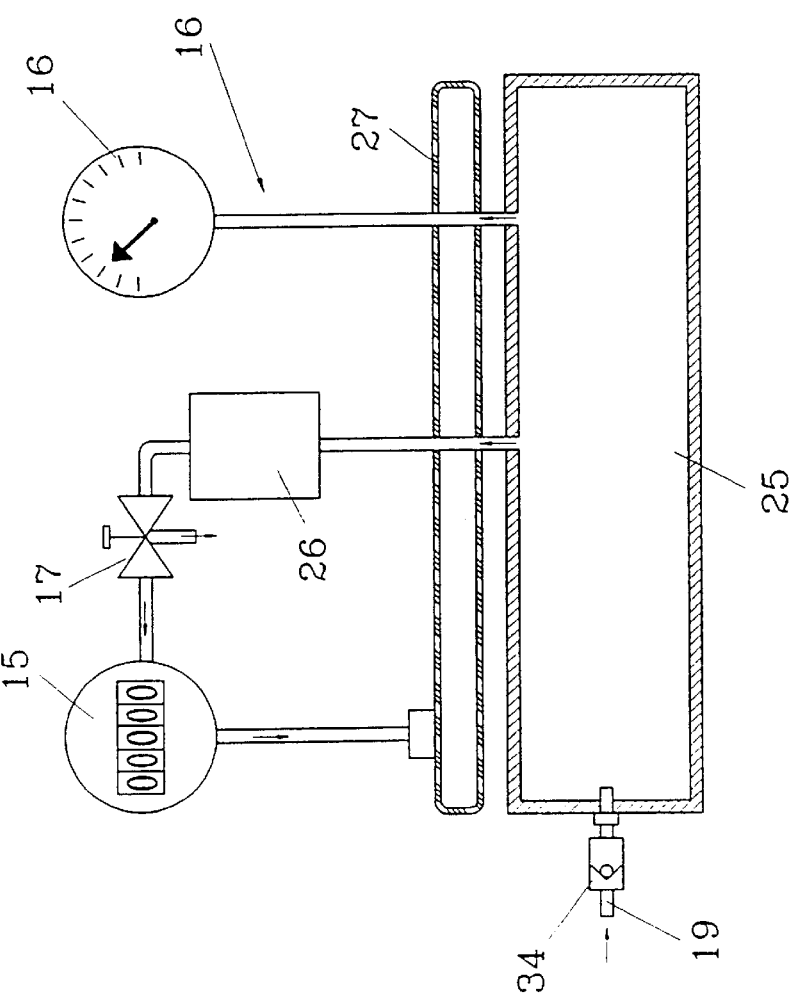
FIG. 6 shows schematically a pressure apparatus with its peripherals included in the infusion apparatus according to FIG. 1.

The function and use of the pressure apparatus 18 will now be described with reference to FIG. 6. It contains a pressure storage chamber 25 in the form of a pressure vessel 14 for compressed air, which storage chamber 25 can be attached to a pump (not shown) via a nipple 19 with a stop valve 34, which pump fills the storage chamber with compressed air, for example at a pressure of 6.5 kg/cm². The pressure gauge 16 shows the pressure in the pressure storage chamber 25. In use, that is, when an infusion bag 21 has been placed in the infusion chamber 13a, the two way valve 17 is opened and compressed air flows to the pressure reduction valve 26 of conventional type. Here the pressure is reduced, for example to 0.15 kg/cm₂, and the pressure chamber 27b is pressurised, whereby the flow meter 15 indicates how much air has been let into the chamber, that being an approximate measure of the amount of infusion liquid that has flowed out of the infusion bag 21. When the infusion bag has been emptied or the infusion terminated, the valve 17 is readjusted so that the interior of the pressure chamber 27b communicates with the atmosphere and air enters it.

Thereafter air can be pumped into the pressure chamber for the next use if not enough air remains in the pressure storage chamber for a second or third infusion.

Because the infusion apparatus is designed to be mobile it can also be equipped with a pump, for example a hand or foot pump to pump air into the pressure storage chamber. It can also be detachable for quick exchange with a pressurised vessel.

Thus emptying the infusion bag is accomplished through the pressure source 27 pressing the bag 21 along its whole length against the top 12. The choice of material in the membrane 27a is very important for achieving an essentially constant outflow rate. It has been found that an elastic balloon is not appropriate for a pressure source because as the balloon is filled more and more energy is expended for expansion of the balloon walls, which means that the outflow rate decreases. By making the membrane of an essentially unstretchable material the outflow from the bag 21 will be nearly constant throughout the whole infusion phase.

This does not solve the problem of the regulation of the flow of infusion liquid to the patient, that is, from the infusion bag 21 to the infusion needle 32.

The tube 24 attached to the bag 21 is equipped in a known way with a needle 33 for perforation of a membrane in the output channel of the bag while the other end of the tube is equipped with a coupling 37, for example in the form of a luer lock coupling 41, as is shown in FIG. 7 and 8. To this end a flow regulating valve 28 is coupled, which in the exemplification according to FIG. 8 has been given a form similar to that of the coupling 37 and which consists of a neck 39 and an inner conical hole 40 to which the luer lock coupling's. 37 male coupling 38 having the same conical form is attached. The other part of the valve is equipped with a luer lock coupling 41 while the conical piece 35 corresponding to the male coupling 38 has a hole 30, for example with a diameter of 0.2–0.5 mm. In the shown exemplification the hole is made of a part of an infusion needle of desired inner diameter moulded in the flow regulating valve 28. Each flow regulating valve 28 thus has an exactly determined hole diameter, on the drawing FIG. 8 indicated by a d, and a given hole length 1 for type of valve. Several flow regulating valves 28 can be arranged in series after each, other possibly with different hole lengths 1 from 3 to 15 mm, but with the same hole diameter, if a greater reduction is desired.

Figure 9:
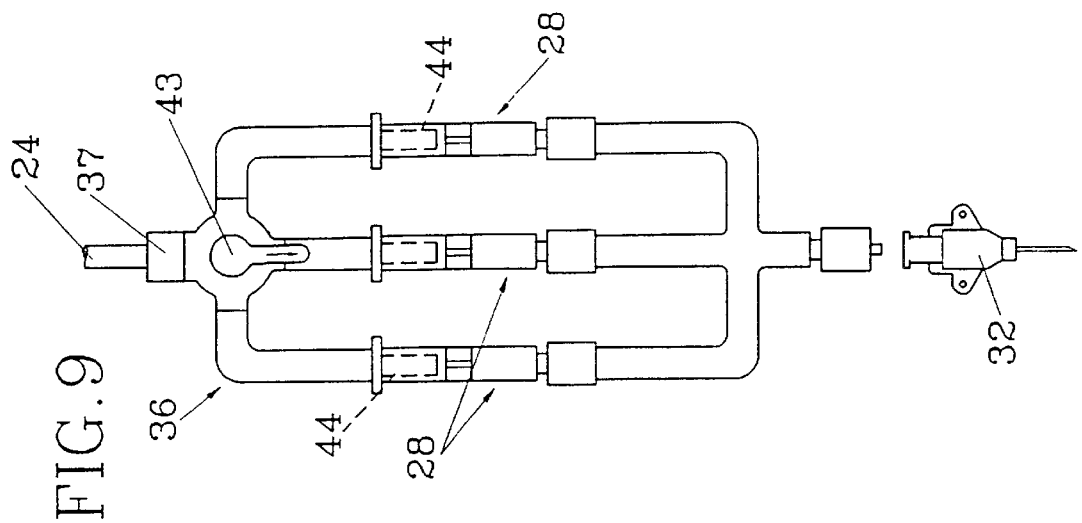
FIG. 9 shows in a view from above an infusion unit in the form of three parallel coupled flow regulating valves for different flow rates per unit time and an infusion needle that can be attached to them.

In different exemplification several valves 28 can be parallel coupled in an infusion unit 36 as is shown in FIG. 9. The unit 36 includes a stop-cock 43 with an input flow opening and three output flow openings each of which is separately attachable to the input flow opening which turn is attachable to the coupling 37 of the output tube 24. One or more flow regulating valves 28 are coupled to each output opening via appropriate filters. By using valves 28 with different flow characteristics, either singly or in series, on the way to the neddle 32 different exactly determined flow rates per unit time can be obtained.

Test carried out with four different flow regulating valves

Flow regulating valves with the following dimensions have been used:

| valve combination | 1 (mm) | d (mm) |
|---|---|---|
| 1 | 5 | 0.3 |
| 2 | 10 | 0.3 |
| 3 | 5 | 0.5 |
| 4 | 10 | 0.5 |

Water pressure corresponding to a water column 80 cm high.

The following flow rates per hour were obtained:

| valve combination | flow (ml/hr) |
|---|---|
| 1 | 400 |
| 2 | 200 |
| 1 + 2 (in series) | 120 |
| 3 | 3200 |
| 4 | 1200 |
| 3 + 4 (in series) | 900 |

For valve combination 1 an infusion bag lasts for 2½ hours.

For valve combination 2 an infusion bag lasts for 5 hours.

For valve combination 3 an infusion bag lasts for about 20 minutes.

For valve combination 4 an infusion bag lasts for about 50 minutes.

For valve combination (3+4) an infusion bag lasts for about 1 hour.

Only flow regulating valves with the same hole diameter should be combined.

The flow regulating valves are thus calibrated to give a certain amount of liquid per unit time.

They can be coupled in series according to FIG. 8 to increase the number of possibilities and they can be marked with clear information. For increased safety color markings can be used.

The flow regulating valves' free ends are coupled to a needle 32 in a vein.

The whole apparatus can then be placed beside the patent on the bed, on a table or something else near the patient. It requires no elevation above the patent and it can also be carried by the patient on a strap or in a bag. No drop indicator is needed. No one is needed to hold the bag when there has been an accident or a catastrophe. It is easy to use for example in an ambulance. Because there is no air in the system air emboli are eliminated and the risk of incorrect dosage is minimal. In most cases the precision is sufficient for dosage of medicines.

Should for some reason the pressure in the pressure storage chamber be exhausted and a pressure source not be available in the vicinity the pressure infusion apparatus can be placed in the conventional manner about 1½ meters above the patient thus ensuring a flow due to gravitational force.

The invention is not limited to the exemplification shown in the diagrams and explained in the text and several variants can be envisaged within the limits of the patent claims. For example the chamber 13 in the housing 11 can be cylindrical with only one opening in the forward end of the housing through which the infusion bag 21 is inserted into the apparatus 10 (the top 13 thus being eliminated).

What is claimed is:

1. A pressure infusion apparatus comprising:
   a housing,
   an infusion chamber,
   at least one infusion bag disposed within the infusion chamber, the infusion bag being adapted to contain liquid and being in fluid communication with an infusion tube,
   at least one flow regulating valve in fluid communication with the infusion tube, the flow regulating valve enabling a calibratable flow of liquid per unit time through the infusion tube, and
   a pressure apparatus adapted for exerting a pressure on the infusion bag so as to supply liquid from the infusion bag to the infusion tube, wherein the pressure apparatus comprises
   a pressure storage chamber, and a pressure source in pneumatic communication with the pressure storage chamber, and
      a pressure reduction valve disposed between the pressure storage chamber and the pressure source, the pressure reduction valve being adapted to significantly reduce a pressure in the pressure source relative to a maximal loading pressure in the pressure storage chamber,
      the pressure source comprising a pressure chamber in pneumatic communication with the pressure storage chamber via the pressure reduction valve, and an unstretchable, air tight, flexible membrane in pneumatic communication with the pressure chamber, the membrane applying the pressure on the infusion bag from the pressure chamber via direct contact of the membrane with the at least one infusion bag, and
   a nipple located on the housing in fluid communication with the pressure storage chamber for recharging the storage chamber with pressure fluid.

2. The pressure infusion apparatus according to claim 1, wherein the pressure storage chamber is adapted to be pumped up with a pump.

3. The pressure infusion apparatus according to claim 2, wherein the pump is separate from the pressure infusion apparatus.

4. The pressure infusion apparatus according to claim 2, wherein the pump is integral to the pressure infusion apparatus.

5. The pressure infusion apparatus according to claim 1, wherein the pressure storage chamber is equipped with a nipple for attachment to an external pressure source.

6. The pressure infusion apparatus according to claim 1, wherein the membrane is attached to an inside of the chamber at about half a height of the chamber, the membrane being so dimensioned that in a passive state the membrane lies against a bottom of the pressure chamber and in a pressurised, inflated state the membrane presses against a top of the chamber.

7. The pressure infusion apparatus according to claim 1, wherein the flow regulating valve is a constant reduction valve with a flow hole having a known ratio of a length of the flow hole to a diameter of the flow hole, the flow hole being 5–10 mm in length and 0.2–0.5 mm in diameter.

8. The pressure infusion apparatus according to claim 5, comprising a plurality of reducing valves coupled in parallel with the infusion unit, wherein each reduction valve is adapted to be separately attachable to a common output via a direction regulating valve, and wherein the length and diameter of the flow hole in each of the reducing valves is different.

9. The pressure infusion apparatus according to claim 7, comprising a plurality of reducing valves coupled in series, wherein the reducing valves have flow holes of equal diameter.

* * * * *